(12) United States Patent
Limon

(10) Patent No.: US 6,325,824 B2
(45) Date of Patent: *Dec. 4, 2001

(54) CRUSH RESISTANT STENT

(75) Inventor: Timothy A. Limon, Cupertino, CA (US)

(73) Assignee: Advanced Cardiovascular Systems, Inc., Santa Clara, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/120,548

(22) Filed: Jul. 22, 1998

(51) Int. Cl.⁷ .......................................................... A61F 2/06
(52) U.S. Cl. ............................................. 623/1.2; 623/1.15
(58) Field of Search ................................ 623/1, 11, 1.15, 623/1.16, 1.17, 1.18, 1.19; 606/198

(56) References Cited

U.S. PATENT DOCUMENTS

| | | |
|---|---|---|
| 4,300,244 | 11/1981 | Bokros . |
| 4,512,338 | 4/1985 | Balko et al. . |
| 4,580,568 | 4/1986 | Gianturco . |
| 4,655,771 | 4/1987 | Wallsten . |
| 4,665,905 | 5/1987 | Jervis . |
| 4,740,207 | 4/1988 | Kreamer . |
| 4,762,128 | 8/1988 | Rosenbluth . |
| 4,795,458 | 1/1989 | Regan . |
| 4,830,003 | 5/1989 | Wolff et al. . |
| 4,856,516 | 8/1989 | Hillstead . |
| 4,878,906 | 11/1989 | Lindemann et al. . |
| 4,886,062 | 12/1989 | Wiktor . |
| 4,893,623 | 1/1990 | Rosenbluth . |
| 4,907,336 | 3/1990 | Gianturco . |
| 4,913,141 | 4/1990 | Hillstead . |
| 4,925,445 | 5/1990 | Sakamoto et al. . |
| 4,935,068 * | 6/1990 | Duerig ................................ 148/11.5 |
| 4,950,227 | 8/1990 | Savin et al. . |
| 4,969,458 | 11/1990 | Wiktor . |
| 4,969,890 | 11/1990 | Sugita et al. . |
| 4,990,155 | 2/1991 | Wilkoff . |
| 4,994,071 | 2/1991 | MacGregor . |
| 4,998,539 | 3/1991 | Delsanti . |
| 5,002,560 | 3/1991 | Machold et al. . |

(List continued on next page.)

FOREIGN PATENT DOCUMENTS

| | | |
|---|---|---|
| 90 10 130 U | 9/1990 | (DE) . |
| 0 423 916 A1 | 4/1991 | (EP) . |
| 0 556 940 A | 8/1993 | (EP) . |
| 0 596 145 A | 5/1994 | (EP) . |
| 0 626 153 | 11/1994 | (EP) . |
| 0 852 933 | 7/1998 | (EP) . |
| WO 95/33422 | 12/1995 | (WO) . |
| WO 96/39998 | 12/1996 | (WO) . |
| WO 96/41592 | 12/1996 | (WO) . |

OTHER PUBLICATIONS

Schetky, L.M., *Shape Memory Alloys*, Scientific American, 281, 74–82, Nov. 1979.

Primary Examiner—David H. Willse
Assistant Examiner—Alvin Stewart
(74) Attorney, Agent, or Firm—Fulwider Patton Lee & Utecht, LLP (57) ABSTRACT

The present invention is directed to a method for maintaining the patency of a vessel via a stent while minimizing both the risk of permanent vessel collapse and the risk of dislodgment of the stent from the implant site if the stent is temporarily deformed due to external forces. The method utilizes a crush-resistant stent having either shape memory or superelastic properties.

25 Claims, 4 Drawing Sheets

U.S. PATENT DOCUMENTS

| | | |
|---|---|---|
| 5,026,377 | 6/1991 | Burton et al. . |
| 5,034,001 | 7/1991 | Garrison et al. . |
| 5,035,706 | 7/1991 | Gianturco et al. . |
| 5,037,392 | 8/1991 | Hillstead . |
| 5,037,427 | 8/1991 | Harada et al. . |
| 5,041,126 | 8/1991 | Gianturco . |
| 5,059,166 | 10/1991 | Fischell et al. . |
| 5,061,275 | 10/1991 | Wallsten et al. . |
| 5,064,435 | 11/1991 | Porter . |
| 5,067,957 | 11/1991 | Jervis . |
| 5,071,407 | 12/1991 | Termin et al. . |
| 5,078,720 | 1/1992 | Burton et al. . |
| 5,089,005 | 2/1992 | Harada . |
| 5,089,006 | 2/1992 | Stiles . |
| 5,092,877 | 3/1992 | Pinchuk . |
| 5,108,416 | 4/1992 | Ryan et al. . |
| 5,123,917 | 6/1992 | Lee . |
| 5,135,517 | 8/1992 | McCoy . |
| 5,158,548 | 10/1992 | Lau et al. . |
| 5,163,952 | 11/1992 | Froix . |
| 5,163,958 | 11/1992 | Pinchuk . |
| 5,171,262 | 12/1992 | MacGregor . |
| 5,183,085 | 2/1993 | Timmermans . |
| 5,190,546 | 3/1993 | Jervis . |
| 5,192,297 | 3/1993 | Hull . |
| 5,197,978 | 3/1993 | Hess . |
| 5,222,969 | 6/1993 | Gillis . |
| 5,222,971 | 6/1993 | Willard et al. . |
| 5,226,913 | 7/1993 | Pinchuk . |
| 5,242,451 | 9/1993 | Harada et al. . |
| 5,256,146 | 10/1993 | Ensminger et al. . |
| 5,258,020 | 11/1993 | Froix . |
| 5,263,964 | 11/1993 | Purdy . |
| 5,282,823 | 2/1994 | Schwartz et al. . |
| 5,282,824 | 2/1994 | Gianturco . |
| 5,292,331 | 3/1994 | Boneau . |
| 5,304,200 | 4/1994 | Spaulding . |
| 5,306,294 | 4/1994 | Winston et al. . |
| 5,345,937 * | 9/1994 | Middleman et al. ................ 128/657 |
| 5,354,308 | 10/1994 | Simon et al. . |
| 5,354,309 | 10/1994 | Schnepp-Pesch et al. . |
| 5,372,600 | 12/1994 | Beyar et al. . |
| 5,378,239 | 1/1995 | Termin et al. . |
| 5,395,390 | 3/1995 | Simon et al. . |
| 5,403,341 | 4/1995 | Solar . |
| 5,405,377 | 4/1995 | Cragg . |
| 5,411,507 | 5/1995 | Heckele . |
| 5,415,664 | 5/1995 | Pinchuk . |
| 5,443,496 | 8/1995 | Schwartz et al. . |
| 5,453,090 | 9/1995 | Martinez et al. . |
| 5,456,694 | 10/1995 | Marin et al. . |
| 5,458,615 | 10/1995 | Klemm et al. . |
| 5,478,349 | 12/1995 | Nicholas . |
| 5,484,444 | 1/1996 | Braunschweiler et al. . |
| 5,496,277 | 3/1996 | Termin et al. . |
| 5,514,154 * | 5/1996 | Lau et al. .............................. 606/195 |
| 5,522,883 | 6/1996 | Slater et al. . |
| 5,534,007 | 7/1996 | St. Germain et al. . |
| 5,554,181 * | 9/1996 | Das .......................................... 623/1 |
| 5,569,295 | 10/1996 | Lam . |
| 5,591,197 * | 1/1997 | Orth et al. ........................... 606/198 |
| 5,597,378 | 1/1997 | Jervis . |
| 5,603,721 * | 2/1997 | Lau et al. .............................. 606/195 |
| 5,628,784 * | 5/1997 | Strecker .................................... 623/1 |
| 5,637,089 | 6/1997 | Abrams et al. . |
| 5,643,339 * | 7/1997 | Kavteladze et al. ...................... 623/1 |
| 5,653,759 * | 8/1997 | Hogan et al. ........................... 623/11 |
| 5,707,376 * | 1/1998 | Kavteladze et al. ................... 606/198 |
| 5,725,570 * | 3/1998 | Heath ........................................ 623/1 |
| 5,800,526 * | 9/1998 | Anderson et al. ........................ 623/1 |
| 5,843,119 * | 12/1998 | Shmulewitz ........................... 606/198 |
| 5,843,164 * | 12/1998 | Frantzen et al. ........................... 623/1 |
| 5,853,419 * | 12/1998 | Imran .................................... 606/191 |
| 6,106,642 * | 8/2000 | DiCarlo et al. ...................... 148/563 |

* cited by examiner

CRUSH RESISTANT STENT

BACKGROUND OF THE INVENTION

The present invention generally relates to self-expanding endoprosthesis devices, in particular self-expanding intraluminal vascular grafts, generally called stents, adapted to be implanted in a body lumen, such as carotid arteries, coronary arteries, peripheral arteries, veins, or other vessels to maintain the patency of the lumen. These devices are frequently used in the treatment of atherosclerotic stenosis in blood vessels especially after percutaneous transluminal angioplasty (PTA) or percutaneous transluminal coronary angioplasty (PTCA) procedures, with the intent to reduce the likelihood of restenosis of a vessel. Stents are also used to support a body lumen, tack-up a flap or dissection in a vessel, or in general where the lumen is weak to add support. The present invention also relates to an intraluminal vascular graft that can be used in essentially any body lumen.

In expandable stents that are delivered with expandable catheters, such as balloon catheters, the stents are positioned over the balloon portion of the catheter and are expanded from a reduced diameter to an enlarged diameter greater than or equal to the inner diameter of the arterial wall, by inflating the balloon. Stents of this type can be expanded to an enlarged diameter by deforming the stent, by engagement of the stent walls with respect to one another, and by one way engagement of the stent walls together with endothelial growth onto and over the stent. Other stents are self-expanding, through the properties of the material constituting the stent or by design. Examples of intravascular stents can be found in U.S. Pat. No. 5,292,331 (Boneau); U.S. Pat. No. 4,580,568 (Gianturco); U.S. Pat. No. 4,856,516 (Hillstead); U.S. Pat. No. 5,092,877 (Pinchuk); and U.S. Pat. No. 5,514,154 (Lau et al.), which are incorporated herein by reference in their entirety.

The problems with some prior art stents, especially those of the expandable type, is that they are often stiff and inflexible. Often, the expandable type stents are formed from stainless steel alloys and the stents are constructed so that they are expanded beyond their elastic limit. Such stents are permanently deformed beyond their elastic limits and are capable of holding open a body lumen and maintaining patency of the body lumen. There are several commercially available stents that are widely used and generally implanted in the coronary arteries after a PTCA procedure.

Stents also are implanted in vessels that are closer to the surface of the body, such as in the carotid arteries in the neck or in peripheral arteries and veins in the leg. Because these stents are so close to the surface of the body they are particularly vulnerable to impact forces that can partially or completely collapse the stent and thereby block fluid flow in the vessel. Since the prior art stents are plastically deformed, once collapsed or crushed they will remain so, permanently blocking the vessel. Thus, the prior art stents can pose an undesirable condition to the patient.

Other forces can impact the prior art stents and cause similar partial or total vessel blockage. Under certain conditions, muscle contractions might cause the prior art stents to partially or totally collapse and restrict blood flow in the vessel in which they are implanted.

Attempts have been made to make stents out of shape memory alloys (see discussion infra), but dislodgment from the implant site may result if these prior art stents are temporarily crushed due to external forces.

What has been needed and heretofore unavailable in the prior art stents is a stent that is formed from a metal alloy having crush-resistant and recovery properties and, importantly, that will not dislodge from the implant site if it is temporarily crushed due to external forces. The present invention satisfies these needs.

SUMMARY OF THE INVENTION

The present invention is directed to a method for maintaining the patency of a body lumen, including providing a substantially cylindrically-shaped stent having crush-resistant superelastic properties; implanting the stent in the body lumen; and providing projections which form on an outer wall surface of the stent and thereby at least partially penetrate the inner wall surface of the body lumen, thus facilitating the attachment of the stent to the inner wall surface of the body lumen so that as an external force is applied to the body lumen, the stent temporarily at least partially collapses, and the stent returns to the substantially cylindrical shape to thereby maintain the patency of the body lumen when the external force is removed.

One object of the present invention is to provide a method of maintaining the patency of a vessel via a stent while minimizing both the risk of permanent vessel collapse and the risk of dislodgment of the stent from the implant site if the stent is temporarily crushed due to external or internal forces. In one preferred method a crush-resistant superelastic stent may be made from a material including a nickel-titanium alloy. The stent of the present invention is placed under stress by collapsing it to a delivery diameter. Once the stent is positioned in a body lumen, it will expand in the radial direction upon a reduction of stress applied to the stent. During expansion of the stent, projections form on the outer wall surface of the stent. These projections at least partially penetrate the inner wall surface of the body lumen. If an external force is then applied to the body lumen, the stent temporarily at least partially collapses. However, due to the projections, the inner surface of the body lumen is held fast to the outer wall surface of the stent. Therefore, the body lumen temporarily collapses with the stent and the stent will not migrate within the body lumen. The stent then quickly regains its former expanded shape due to its superelastic qualities.

In another preferred method, the stent may be constructed of a shape memory alloy, such as a nickel-titanium alloy. The stent is designed to expand in the radial direction when inserted into a body lumen and upon reaching a transition temperature that is below normal body temperature. The stent further exhibits crush-resistant superelastic qualities. Again, during expansion of the stent, projections form on the outer wall surface of the stent. These projections at least partially penetrate the inner wall surface of the body lumen. If an external force is then applied to the body lumen, the stent temporarily at least partially collapses. However, due to the projections, the inner surface of the body lumen is held fast to the outer wall surface of the stent. Therefore, the body lumen temporarily collapses with the stent and the stent will not migrate within the body lumen. The stent then quickly regains its former expanded shape due to its superelastic qualities.

Other features and advantages of the present invention will become more apparent from the following detailed description of the invention when taken in conjunction with the accompanying exemplary drawings.

DETAILED DESCRIPTION OF THE PREFERRED EMBODIMENTS

During PTCA procedures it is common to use a dilation catheter to expand a diseased area to open the patient's lumen so that blood freely flows. Despite the beneficial aspects of PTCA procedures and its widespread and accepted use, it has several drawbacks, including the possible development of restenosis and perhaps acute thrombosis and sub-acute closure. This recurrent stenosis has been estimated to occur in seventeen to fifty percent of patients despite the initial PTCA procedure being successful. Restenosis is a complex and not fully understood biological response to injury of a vessel which results in chronic hyperplasia of the neointima. This neointimal hyperplasia is activated by growth factors which are released in response to injury. Acute thrombosis is also a result of vascular injury and requires systemic antithrombotic drugs and possibly thrombolytics as well. This therapy can increase bleeding complications at the catheter insertion site and may result in a longer hospital stay. Sub-acute closure is a result of thrombosis, elastic recoil, and/or vessel dissection.

Several procedures have developed to combat restenosis and sub-acute or abrupt closure, one of which is the delivery and implanting of an intravascular stent. Stents are widely used throughout the United States and in Europe and other countries. Generally speaking, the stents can take numerous forms, however, most common is a generally cylindrical hollow tube that holds open the vascular wall at the area that has been dilated by a dilation catheter. One highly regarded stent used and sold in the United States is sold under the tradename ACS Multi-Link Stent, which is made by Advanced Cardiovascular Systems, Inc., Santa Clara, Calif.

The stents of the present invention can have virtually any configuration that is compatible with the body lumen in which they are implanted. The stent should be configured so that there is a substantial amount of open area and preferably the open area to metal ratio is at least 80%. The stent also should be configured so that dissections or flaps in the body lumen wall are covered and tacked up by the stent.

Figure 1:
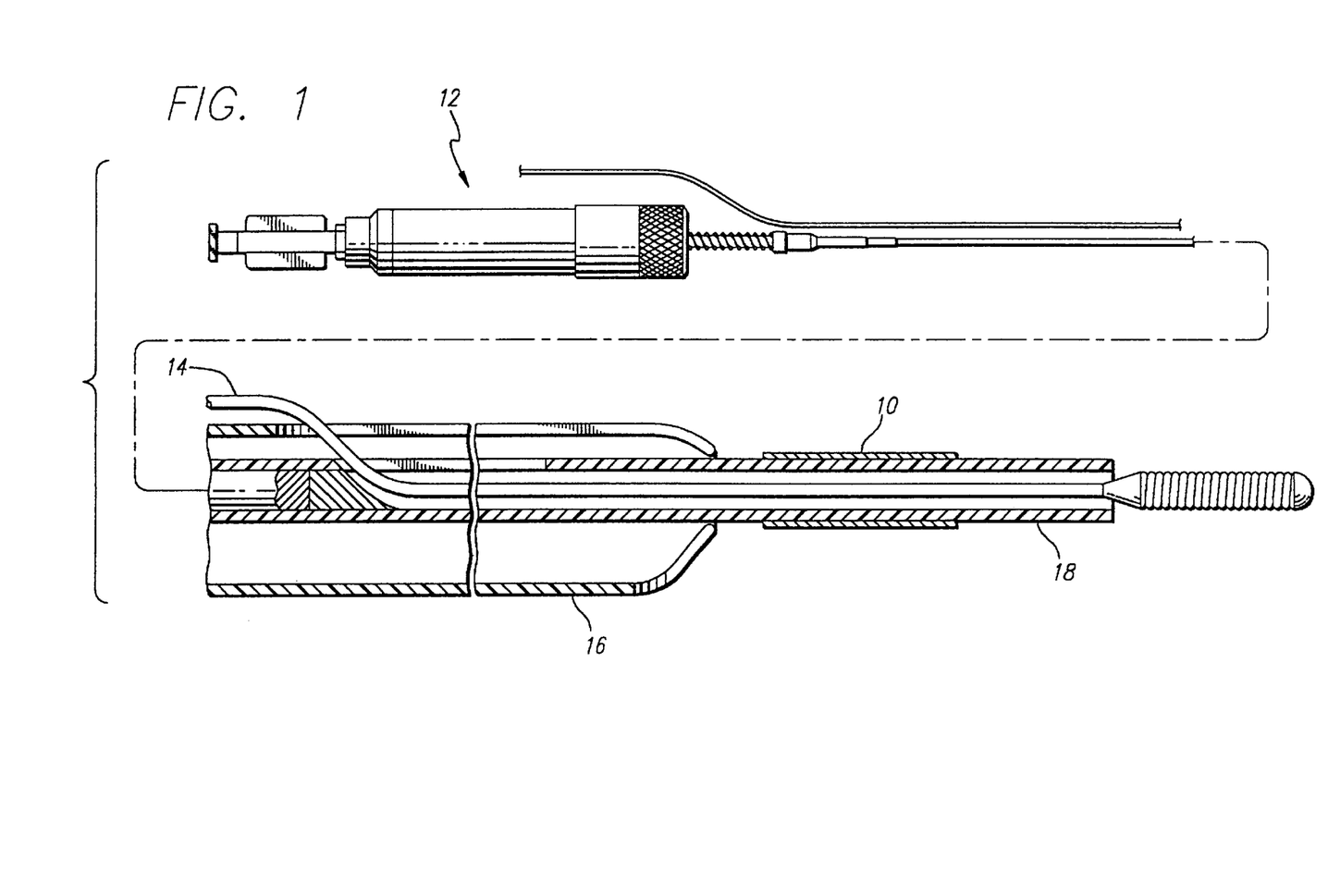
FIG. 1 is a partial cross-sectional view of a stent delivery system.

Referring to FIG. 1, in one preferred embodiment, stent 10 of the present invention is formed partially or completely of alloys such as Nitinol (NiTi) which have superelastic (SE) characteristics.

The stent is modeled after the stent disclosed in U.S. Pat. No. 5,569,295, "Expandable Stents and Method for Making Same," issued to Lam on Oct. 29, 1996, which is incorporated herein by reference in its entirety, with the main difference being that the stent of the present invention is constructed of a superelastic material. The configuration of the stent is just one example of many stent configurations that may be used in the method of the present invention.

Superelastic refers to an isothermal reaction; i.e., stress-induced martensite (SIM). Alloys having superelastic properties generally have at least two phases: a martensite phase, which has a relatively low tensile strength and which is stable at relatively low temperatures, and an austenite phase, which has a relatively high tensile strength and which is stable at temperatures higher than the martensite phase. Superelastic characteristics generally allow the metal stent to be deformed by collapsing and deforming the stent and creating stress which causes the NiTi to change to the martensite phase. The stent is restrained in the deformed condition to facilitate the insertion into a patient's body, with such deformation causing the phase transformation. Once within the body lumen, the restraint on the stent is removed, thereby reducing the stress therein so that the superelastic stent can return to its original undeformed shape by the transformation back to the austenite phase.

FIG. 1 illustrates a rapid exchange stent delivery system that includes a manipulating device 12, a guidewire 14, a delivery sheath 16, and an intravascular catheter 18. This delivery system is just one example of a delivery system that may be used with the present invention. More details of this type of delivery system may be found in U.S. Pat. No. 5,458,615, "Stent Delivery System," issued to Klemm et al. on Oct. 17, 1995, which is incorporated herein by reference in its entirety. Other delivery systems, such as well-known over-the-wire delivery systems, may be used without departing from the scope of the invention.

Figure 2:
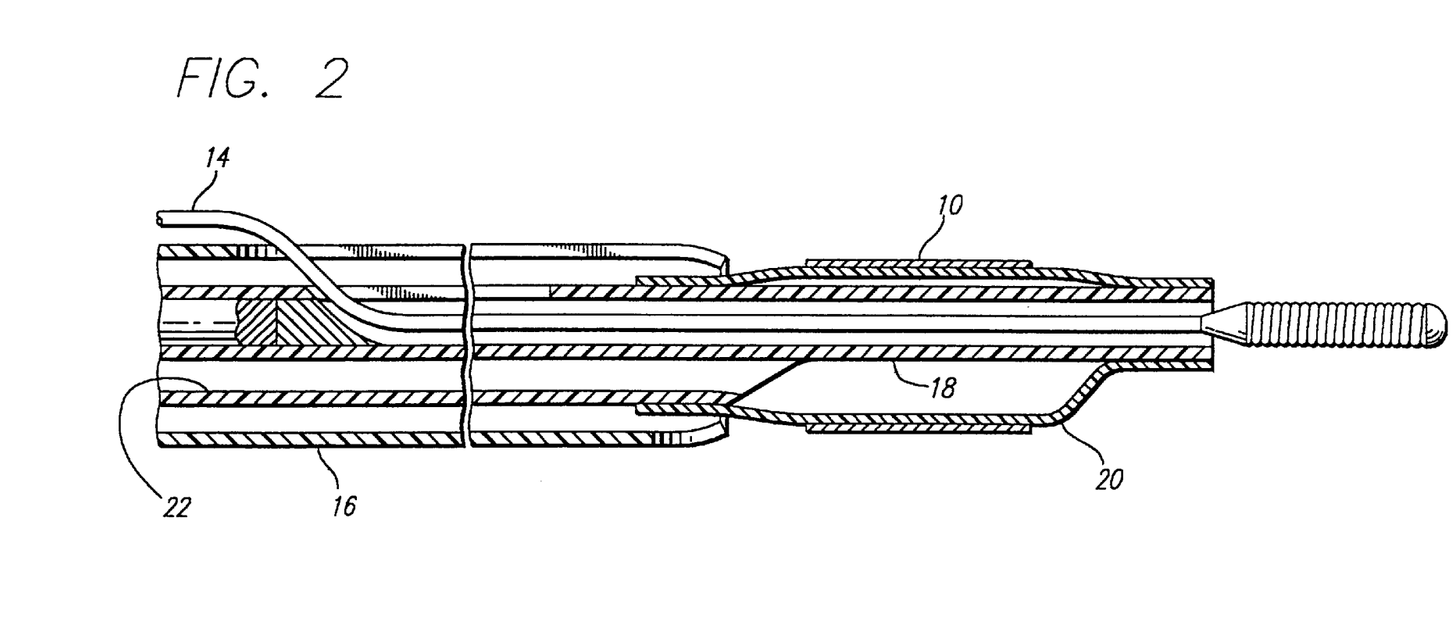
FIG. 2 shows the stent delivery system of FIG. 1 with an optional expandable balloon.

FIG. 2 depicts a variation on the delivery system of FIG. 1, and includes an expandable balloon 20 and balloon inflation lumen 22.

Figure 3:
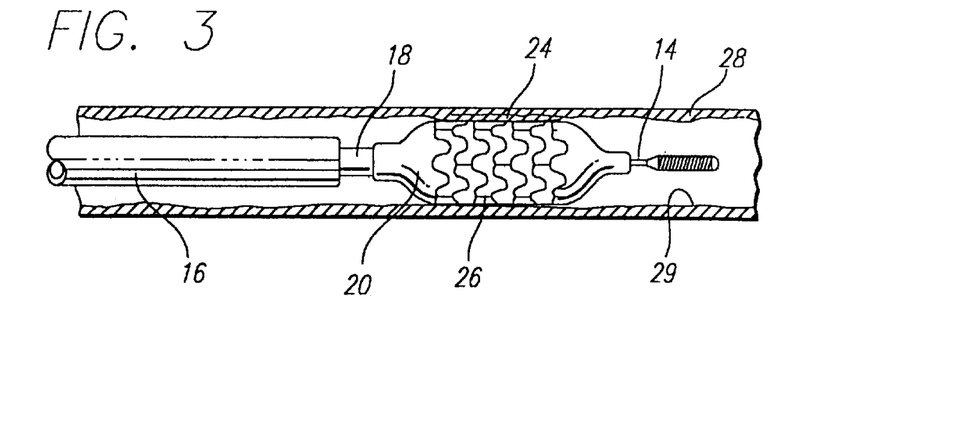
FIG. 3 is an elevational view, partially in section, depicting a stent mounted on a delivery catheter and expanded within a damaged vessel, pressing a damaged vessel lining against the vessel wall.

In keeping with the invention, and turning to FIG. 3, stent 10 preferably includes a plurality of radially expandable cylindrical elements 24 disposed generally coaxially and interconnected by members 26 disposed between adjacent cylindrical elements 24. The stent is formed from a superelastic material such as NiTi and undergoes an isothermal reaction when stressed. The stent is first compressed to a delivery diameter, thereby creating stress in the NiTi alloy so that the NiTi is in a martensitic state having relatively low tensile strength. In the martensitic phase, the stent is mounted onto a catheter by known methods such as adhesives, or other restraining means. Alternatively, the stent can be mounted within delivery sheath 16 so that the stent, which is biased radially outwardly, is pushing radially outwardly against the sheath. In its delivery diameter, the overall diameter of the stent and catheter are less than the inside diameter of artery 28 or the vessel in which they are inserted. After the stent is inserted into the artery or other vessel, the stress upon the stent may be removed by withdrawing the delivery sheath in a proximal direction, whereupon the stent immediately expands and returns to its original undeformed shape by the transformation back to the more stable austenite phase. If expandable balloon 20 of FIG. 2 is implemented, the stent may be further expanded by inflation of the expandable balloon via balloon inflation lumen 22 by known methods.

Figure 4:
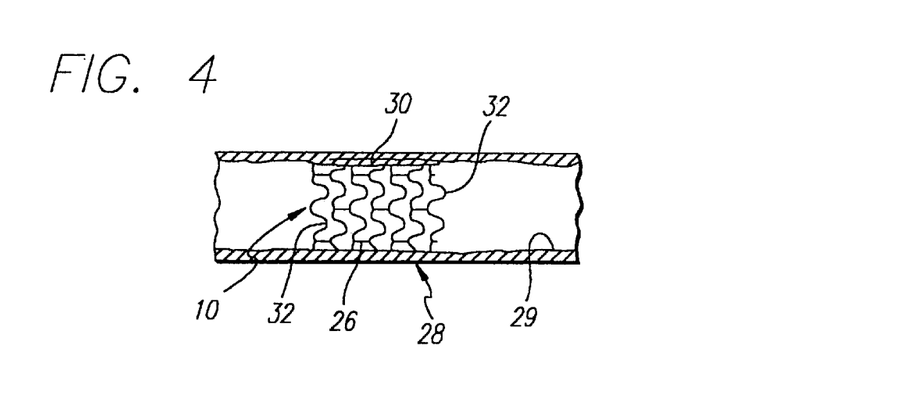
FIG. 4 is an elevational view, partially in section, depicting the expanded stent within the vessel after withdrawal of the delivery catheter.

FIG. 4 illustrates stent 10 in the expanded condition after the delivery system has been removed. As the stent expands from the delivery diameter to the expanded diameter, peaks 32 simultaneously form into projections 34 (see FIG. 5) on the outer wall surface of the stent and at least partially penetrate the inner wall surface of artery 28 or other body lumen. If an external force is then applied to the artery, the stent temporarily at least partially collapses or deforms. As the stent deforms, stress in the NiTi alloy causes a phase transformation from the austenite to the martensite phase.

Figure 5:
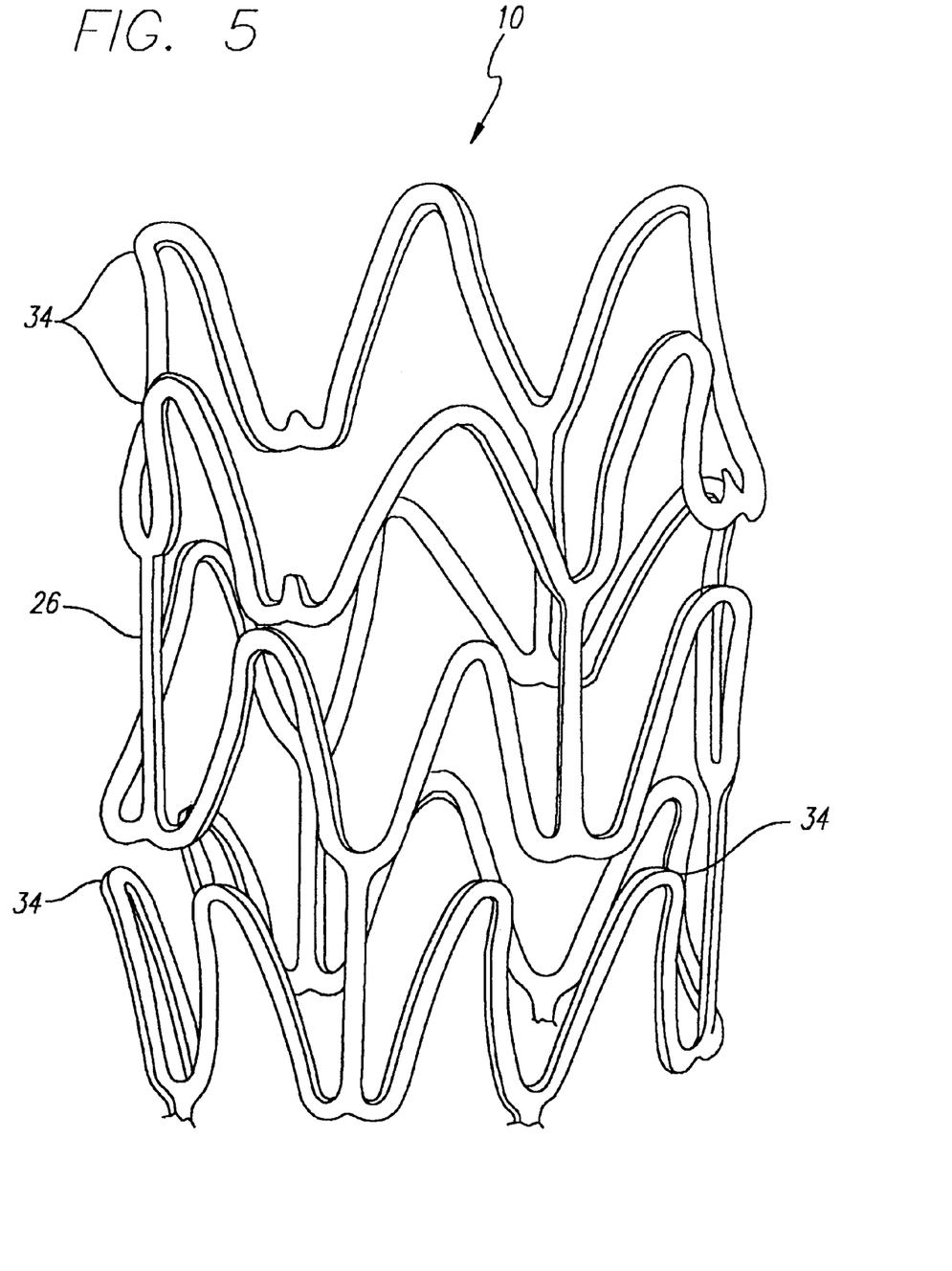
FIG. 5 is a view of a portion of the stent in the expanded condition.

Due to the projections on the outer wall surface of the stent embedding in arterial wall 29, the artery temporarily collapses with the stent and the stent will not migrate within the artery. When the external force is removed, the stress in the stent is removed so that the stent quickly transforms back from the martensite to the austenite phase so that the stent is fully expanded and the artery remains open. Thus, the crush-resistant superelastic stent is implanted in an artery, thereby maintaining the patency of the artery while minimizing both the risk of permanent arterial collapse and the risk of dislodgment of the stent from the implant site if the stent is temporarily deformed due to external forces.

When stress is applied to a specimen of a metal such as Nitinol exhibiting superelastic characteristics at a temperature at or above which the transformation of the martensite phase to the austenite phase is complete, the specimen deforms elastically until it reaches a particular stress level where the alloy then undergoes a stress-induced phase transformation from the austenite phase to the martensite phase. As the phase transformation proceeds, the alloy undergoes significant increases in strain, but with little or no corresponding increases in stress. The strain increases while the stress remains essentially constant until the transformation of the austenite phase to the martensite phase is complete. Thereafter, further increase in stress is necessary to cause further deformation. The martensitic metal first yields elastically upon the application of additional stress and then plastically with permanent residual deformation.

If the load on the specimen is removed before any permanent deformation has occurred, the martensitic specimen will elastically recover and transform back to the austenite phase. The reduction in stress first causes a decrease in strain. As stress reduction reaches the level at which the martensite phase transforms back into the austenite phase, the stress level in the specimen will remain essentially constant (but substantially less than the constant stress level at which the austenite transforms to the martensite) until the transformation back to the austenite phase is complete; i.e., there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as superelasticity or pseudoelasticity.

The prior art makes reference to the use of metal alloys having superelastic characteristics in medical devices which are intended to be inserted or otherwise used within a patient's body. See, for example, U.S. Pat. No. 4,665,905 (Jervis) and U.S. Pat. No. 4,925,445 (Sakamoto et al.), which are incorporated by reference herein in their entirety.

Figure 6:
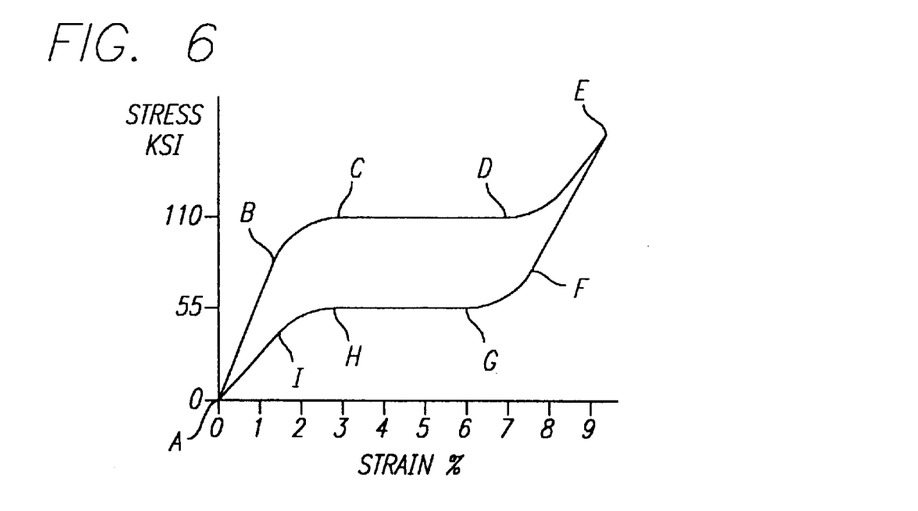
FIG. 6 is a schematic, graphical illustration of a typical stress-strain relationship of superelastic material.

FIG. 6 illustrates an example of a preferred stress-strain relationship of an alloy specimen, such as stent 10, having superelastic properties as would be exhibited upon tensile testing of the specimen. The line from point A to point B thereon represents the elastic deformation of the specimen. After point B the strain or deformation is no longer proportional to the applied stress and it is in the region between point B and point C that the stress-induced transformation of the austenite phase to the martensite phase begins to occur. There can be an intermediate phase developed, sometimes called the rhombohedral phase, depending upon the composition of the alloy. At point C the material enters a region of relatively constant stress with significant deformation or strain. It is in this region that the transformation from austenite to martensite occurs. At point D the transformation to the martensite phase due to the application of tensile stress to the specimen is substantially complete. Beyond point D the martensite phase begins to deform, elastically at first, but, beyond point E, the deformation is plastic or permanent.

When the stress applied to the superelastic metal is removed, the metal will recover to its original shape, provided that there was no permanent deformation to the martensite phase. At point F in the recovery process, the metal begins to transform from the stress-induced, unstable martensite phase back to the more stable austenite phase. In the region from point G to point H, which is also an essentially constant stress region, the phase transformation from martensite back to austenite is essentially complete. The line from point I to the starting point A represents the elastic recovery of the metal to its original shape.

The superelastic alloy is preferably formed from an alloy consisting essentially of about 30% to about 52% titanium and the balance nickel and up to 10% of one or more additional alloying elements. Such other alloying elements may be selected from the group consisting of up to 3% each of iron, cobalt, platinum, palladium, and chromium, and up to about 10% copper and vanadium. As used herein, all references to percent composition are atomic percent unless otherwise noted.

In another preferred embodiment, a NiTi stent with SME (shape memory effect) is heat-treated at approximately 500° C. The stent is mechanically deformed into a first, smaller diameter for mounting on a catheter delivery system, such as the delivery system of FIG. 2, that includes expandable balloon 20 and balloon inflation lumen 22. After the stent has been expanded by the balloon and deployed against arterial wall 29 of artery 28, 45° C. heat is applied causing the stent to return to its fully expanded larger diameter and be in contact with the arterial wall of the artery. The application of 45° C. of heat is compatible with most applications in the human body, but it is not to be limited to this temperature as higher or lower temperatures are contemplated without departing from the invention. The 45° C. temperature can be achieved in a conventional manner well known in the art such as by warm saline injected into the delivery catheter and balloon.

The shape memory characteristics allow the devices to be deformed to facilitate their insertion into a body lumen or cavity and then be heated within the body so that the device returns to its original shape. Again, alloys having shape memory characterisitcs generally have at least two phases: a martensite phase, which has a relatively low tensile strength and which is stable at relatively low temperatures, and an austenite phase, which has a relatively high tensile strength and which is stable at temperatures higher than the martensite phase.

Shape memory characteristics are imparted to the alloy by heating the metal at a temperature above which the transformation from the martensite phase to the austenite phase is complete; i.e., a temperature above which the austenite phase is stable. The shape of the metal during this heat treatment is the shape "remembered." The heat-treated metal is cooled to a temperature at which the martensite phase is stable, causing the austenite phase to transform to the martensite phase. The metal in the martensite phase is then plastically deformed, e.g., to facilitate the entry thereofinto a patient's body. Subsequent heating of the deformed martensite phase to a temperature above the martensite to austenite transformation temperature causes the deformed martensite phase to transform to the austenite phase. During this phase transformation the metal reverts back to its original shape.

The recovery or transition temperature may be altered by making minor variations in the composition of the metal and in processing the material. In developing the correct composition, biological temperature compatibility must be determined in order to select the correct transition temperature. In other words, when the stent is heated, it must not be so hot that it is incompatible with the surrounding body tissue. Other shape memory materials may also be utilized, such as, but not limited to, irradiated memory polymers such as autocrosslinkable high density polyethylene (HDPEX).

Shape memory alloys are known in the art and are discussed in Shape Memory Alloys, *Scientific American*, Volume 281, pages 74–82 (November 1979), incorporated herein by reference.

Shape memory alloys undergo a transition between an austenitic state and a martinsitic state at certain temperatures. When they are deformed while in the martinsitic state they will retain this deformation as long as they are retained in this state, but will revert to their original configuration when they are heated to a transition temperature, at which time they transform to their austenitic state. The temperatures at which these transitions occur are affected by the nature of the alloy and the condition of the material. Nickel-titanium-based alloys (NiTi), wherein the transition temperature is slightly lower than body temperature, are preferred for the present invention. It is desirable to have the transition temperature set at just below body temperature to insure a rapid transition from the martinsitic state to the austenitic state when the stent is implanted in a body lumen.

Turning again to FIG. 3, stent 10 is formed from a shape memory alloy, such as NiTi discussed supra. After the stent is inserted into artery 28 or other vessel, expandable balloon 20 is inflated via balloon inflation lumen 22 by conventional means such that the stent is expanded radially outwardly. The stent then immediately expands due to contact with the higher temperature within artery 28 as described for devices made from shape memory alloys. Again, peaks 32 simultaneously form into projections 34 (see FIG. 5) on the outer wall surface of the stent and at least partially penetrate arterial wall 29 of the artery or other body lumen. Again, if an external force is then applied to the artery, the stent temporarily at least partially collapses. However, due to the projections, the inner surface of the artery is held fast to the outer wall surface of the stent. Therefore, the artery temporarily collapses with the stent and the stent will not migrate within the artery. The stent then quickly regains its former expanded shape due to its shape memory qualities. Thus, the crush-resistant stent, having shape memory characteristics, is implanted in a vessel, thereby maintaining the patency of a vessel while minimizing both the risk of permanent vessel collapse and the risk of dislodgment of the stent from the implant site if the stent is temporarily deformed due to external forces.

While the invention has been illustrated and described herein in terms of its use as a method for maintaining the patency of a vessel via a stent while minimizing both the risk of permanent vessel collapse and the risk of dislodgment of the stent from the implant site if the stent is temporarily crushed due to external forces, it will be apparent to those skilled in the art that the invention can be used in other instances. Other modifications and improvements may be made without departing from the scope of the invention.

What is claimed is:

1. A method for maintaining the patency of a body lumen, comprising:

providing a substantially cylindrically-shaped stent having crush-resistant superelastic properties;

implanting the stent in the body lumen;

providing projections which form on an outer wall surface of the stent and thereby at least partially penetrate an inner wall surface of the body lumen, thus facilitating the attachment of the stent to the inner wall surface of the body lumen so that as an external force is applied to the body lumen, the stent will not migrate and the stent temporarily at least partially collapses, the stent returning to the substantially cylindrical shape to thereby maintain the patency of the body lumen when the external force is removed; and inducing formation of the projections through an isothermal phase transformation.

2. The method of claim 1, wherein the stent is in an austenite phase at body temperature, and transforms to a martensite phase when subjected to stress.

3. The method of claim 1, wherein the stent is made from a superelastic material including a nickel-titanium alloy.

4. The method of claim 1, wherein the stent is made from a superelastic alloy consisting essentially of about 40 to about 49% titanium and the balance nickel and up to 10% of other alloying elements.

5. The method of claim 4, wherein the other alloying elements are selected from the group consisting of iron, cobalt, vanadium, and copper.

6. The method of claim 5, wherein the alloy contains vanadium or copper in amounts up to about 10% and up to about 3% of iron, cobalt, vanadium, and copper.

7. The method of claim 2, wherein the strain of the superelastic material during the transformation from the austenite phase to the martensite phase is within the range of about 2% to about 8%.

8. The method of claim 7, wherein the austenite-to-martensite transformation occurs at a relatively constant yield stress above about 50 ksi.

9. The method of claim 7, wherein the austenite-to-martensite transformation occurs at a relatively constant yield stress above about 70 ksi.

10. The method of claim 7, wherein the austenite-to-martensite transformation occurs at a relatively constant yield stress above about 90 ksi.

11. The method of claim 1, wherein the stent is made from a shape memory alloy including a nickel-titanium alloy, the method further comprising providing a transition temperature for the nickel-titanium alloy that is below normal body temperature.

12. The method of claim 1, wherein the stent is formed from a metal alloy selected from the group of metal alloys consisting of stainless steel, nickel-titanium, nickel-copper-titanium, nickel-titanium-vanadium, titanium-nickel-cobalt, copper-zinc, copper-zinc-aluminum, copper-zinc-gallium, copper-zinc-tin, copper-zinc-silicon, copper-aluminum-nickel, copper-aluminum-zinc, copper-tin, gold-cadmium, nickel-aluminum, iron-platinum, and nickel-titanium-X where X is a ternary element, the method further comprising providing a transition temperature for the alloy that is below normal body temperature.

13. The method of claim 1, wherein the projections form on the outer wall surface of the stent when the stent reaches a transition temperature.

14. The method of claim 1, wherein the stent transforms from a martensitic state to an austenitic state at a transition temperature thereby expanding the stent radially outward and simultaneously forming the projections on the outer wall surface of the stent.

15. The method of claim 1, wherein the application of the external force includes muscle contractions surrounding the body lumen where the stent is implanted.

16. The method of claim 1, wherein the application of the external force includes an impact force from outside the patient's body applied in the area of the stent thereby at least partially collapsing the stent until the external force is removed.

17. A method for maintaining the patency of a body lumen, comprising:
   providing a substantially cylindrically-shaped stent having crush-resistant superelastic properties;
   implanting the stent in the body lumen;
   providing projections that form on an outer wall surface of the stent;
   inducing formation of the projections through an isothermal phase transformation;
   wherein the stent is formed from a metal alloy selected from the group of metal alloys consisting of copper-zinc, copper-zinc-aluminum, copper-zinc-gallium, copper-zinc-tin, copper-zinc-silicon, copper-aluminum-nickel, copper-aluminum-zinc, copper-tin, gold-cadmium, nickel-aluminum, or iron-platinum.

18. A stent for maintaining the patency of a body lumen, comprising:
   a cylindrically shaped body having an outer wall surface, and including a plurality of cylindrical elements arranged coaxially;
   connecting members interconnecting adjacent cylindrical elements;
   wherein the stent includes a superelastic alloy that undergoes a first isothermal phase transformation when stressed; and
   projections formed in the outer wall surface through a second isothermal phase transformation during expansion of the stent.

19. The stent of claim 18, wherein the first isothermal phase transformation includes a reversible transformation from an austenitic phase to a martensitic phase.

20. The stent of claim 18, wherein the second isothermal phase transformation includes a reversible transformation from a martensitic phase to an austenitic phase.

21. The stent of claim 18, wherein the superelastic alloy includes nickel, titanium, and a third element selected from the group of elements consisting of: iron, cobalt, platinum, palladium, chromium, copper, or vanadium.

22. The stent of claim 21, wherein the third element includes up to 3 atomic percent of one of iron, cobalt, platinum, palladium, and chromium.

23. The stent of claim 21, wherein the third element includes up to 10 atomic percent of one of copper and vanadium.

24. The stent of claim 18, wherein the superelastic alloy includes 30 to 52 atomic percent titanium and up to 10 atomic percent of a third element.

25. The stent of claim 18, wherein the projections extend from the outer wall surface and penetrate the body lumen.

* * * * *